US006194197B1

(12) United States Patent
Hyman et al.

(10) Patent No.: US 6,194,197 B1
(45) Date of Patent: Feb. 27, 2001

(54) BIOREMEDIATION OF XENOBIOTICS INCLUDING METHYL TERT-BUTYL ETHER

(75) Inventors: Michael R. Hyman; Kenneth Williamson; Lynda M. Ciuffetti, all of Corvallis, OR (US)

(73) Assignee: The State of Oregon Acting by and through the State Board of Higher Education on Behalf of Oregon State University, Corvallis, OR (US)

( * ) Notice: Subject to any disclaimer, the term of this patent is extended or adjusted under 35 U.S.C. 154(b) by 0 days.

(21) Appl. No.: 09/038,754

(22) Filed: Mar. 11, 1998

Related U.S. Application Data
(60) Provisional application No. 60/040,776, filed on Mar. 14, 1997.

(51) Int. Cl.$^7$ ...................................................... B09B 3/00
(52) U.S. Cl. ..................................... 435/262.5; 435/254.1
(58) Field of Search ................................ 435/262, 262.5, 435/254.1

(56) References Cited

U.S. PATENT DOCUMENTS 5,814,514 * 9/1998 Steffan et al. ........................ 435/262

OTHER PUBLICATIONS

Abstract, Hardison et al., Applied and Environmental Microbiology, vol. 63, No. 8, 3059–3067, 1997.*

Steffan et al., Biodegradation of the Gasoline Oxygenates Methyl tert–Butyl Ether, Ethyl tert–Bultyl Ether, and tert–Amyl Methyl Ether by Propane–Oxidizing Bacteria, Applied and Environmental Microbiology, 63:4216–4222, 1997.

Davies et al., Hyphomycetes utilizing natural gas, Can. J. Microbiol., 19:81–85, 1973.

Sariaslani, Microbial Cytochromes P–450 and Xenobiotic Metabolism, Advances in Applied Microbiology, 36:133–178, 1991.

Brady et al., Metabolism of methyl tertiary–butyl ether by rat hepatic microsomes, Arch. Toxicol. (1990) 64:157–160, 1990.

Parales et al., Degradation of 1,4–Dioxane by an Actinomycete in Pure Culture, Applied and Environmental Microbiology, 60:4527–4530, 1994.

Mo et al., Biodegradation of methyl t–butyl ether by pure bacterial cultures, Appl. Microbiol Biotechnicol, 47:69–72, 1997.

Steffan et al., Biodegradation of Methyl tert–Butyl Ether (MTBE), Environmetal and General Applied Microbiology, Q–372, Apr., 1997, p. 517.

McCarty, In situ bioremediation of chlorinated solvents, Currrent Opinion in Biotechnology, 4:323–330, 1993.

Heydeman et al., Growth of Soil Bacteria on Diethyl Ether, Toxicological Profile for Methyl tert–Butyl Ether, Journal of General Microbiology, 81:ix–x, 1974.

Mumtaz et al., Toxicological Profile for Methyl tert–Butyl Ether, U.S. Department of Health and Human Services Report, 1994.

* cited by examiner

Primary Examiner—David A. Redding
(74) Attorney, Agent, or Firm—Klarquist Sparkman Campbell Leigh & Whinston, LLP

(57) ABSTRACT

Microorganisms capable of co-metabolizing methyl tert-butyl ether are disclosed, along with methods for selecting microorganisms possessing such activity. Methods for bioremediation of MTBE-contaminated media and biofilter systems are also disclosed.

8 Claims, 12 Drawing Sheets

Activated Sludge

Rotating Biological Contactor

Fluidized Bed Biofilm Reactor

BIOREMEDIATION OF XENOBIOTICS INCLUDING METHYL TERT-BUTYL ETHER

PRIORITY CLAIM

This application claims priority to co-pending U.S. provisional patent application serial No. 60/040,776, filed on Mar. 14, 1997, which is incorporated herein by reference.

FIELD OF THE INVENTION

The present invention relates to the bioremediation of xenobiotic compounds, in particular the gasoline additive methyl tert-butyl ether (MTBE), by microorganisms including Graphium sp. fungi. Biofilters that incorporate such organisms and that may be used to reduce MTBE contamination in, for example, ground water, are also disclosed.

BACKGROUND OF THE INVENTION

The ether bond has recently been described as "the single most common and unifying structural feature which confers to both biological and xenobiotic compounds a high degree of resistance to biological mineralization" (White et al., 1996). This resistance occurs in ether-bonded compounds ranging from the complex natural product lignin, to simpler and widely used anthropogenic chemicals including several pesticides (Alexander, 1973), common solvents such as diethyl ether (DEE) (Alexander, 1973) and, more recently, gasoline additives such as methyl tert-butyl ether (MTBE) (Mormille et al., 1994; Yeh and Novak, 1994), tert-amyl methyl ether (TAME) and ethyl tert-butyl ether (ETBE). At present very little is known about the microbial degradation of simple alkyl ethers. For instance, there are only two reports of microorganisms utilizing DEE as a growth-supporting substrate but these reports did not investigate the possibility of growth-supporting contaminants (Heyden, 1974; Parales et al., 1994) (the importance of this issue has been recently illustrated by the observation that growth of Ancyclobacter aquaticus in the presence of 2-chloroethyl vinyl ether is supported by abiotic hydrolysis products of the ether rather than the ether compound itself (van den Wijngaard et al., 1993)).

Whereas DEE is used as an industrial solvent, MTBE is widely used in many modem gasoline formulations. MTBE acts as both an octane enhancer and as an oxygenating compound, thereby permitting both an elimination of alkyl-lead anti-knocking agents and a reduction in automobile carbon monoxide emissions. Current consumption of MTBE in the United States, the world's largest consumer, was recently estimated at approximately $2.0 \times 10^{10}$ gallons/year (Ainsworth, 1991). There is currently considerable uncertainty about the long-term human health effects of MTBE exposure. The U.S. Environmental Protection Agency has issued a drinking-water advisory for MTBE of 20–40 $\mu$g/l USEPA (1997) (Drinking Water Advisory: Consumer acceptability advice and health effects analysis on methyl tertiary-butyl ether (MtBE) Office of Water, EPA-822-F-97-009. USEPA, Washington, D.C.). Recently, MTBE has been detected in many urban groundwater supplies, most likely as the result of gasoline spills and leaking storage tanks (Squillace et al., 1996). Recent studies also indicate that MTBE is very poorly biodegradable in groundwater under a variety of redox conditions (Mormille et al., 1994; Yeh and Novak, 1994). MTBE degradation has been described for a mixed microbial culture in a pathway involving tert-butyl alcohol (TBA) (Salanitro et al., 1994). Three bacterial isolates have been reported to exhibit slow growth on MTBE and yeast extract (Mo et al., 1997) and the oxidation of MTBE by propane-oxidizing bacteria such as *Mycobacterium vaccae* has been described (Steffan et al., 1997). However, the affinity of these organisms for MTBE (or, more specifically, the $K_m$ of the MTBE degrading enzymes produced by these organisms) may not be sufficient to achieve the 20–40 $\mu$g/l standard set by the EPA for MTBE levels in water.

It is an objective of the present invention to provide isolated microorganisms which degrade MTBE and/or chlorinated aliphatic hydrocarbons, and which have a high affinity for these compounds.

It is a further object of this invention to provide biofilters suitable for the bioremediation of MTBE.

SUMMARY OF THE INVENTION

The present invention rests, in part, on the discovery that certain microorganisms possess the ability to co-metabolize MTBE. In one example, Graphium sp. fungus is shown to co-metabolize MTBE when grown in the presence of gaseous n-alkanes such as ethane, propane and n-butane and simple branched alkanes such as isobutane (2-methyl propane) and isopentane (2-methyl butane). It is shown that the ability of Graphium to degrade MTBE is likely attributable to the expression of a non-specific cytochrome P-450 oxygenase activity. This activity is known to be found in a number of microorganisms, including other fungi and bacteria. Accordingly, it is anticipated that a wide range of microorganisms possess the capability to co-metabolize MTBE and other gasoline additions such as TAME and ETBE. One aspect of the present invention is thus a method of selecting a microorganism capable of co-metabolizing MTBE, wherein a pure culture of the microorganism is grown in a suitable growth medium and supplied with a sufficient amount of at least one gaseous n-alkane or simple branched alkane. MTBE is then added to the growth medium, and the growth medium is then assayed to quantify MTBE degradation. The assay permits selection of MTBE degrading microorganisms. In one embodiment, this assay step is performed by detecting the presence of MTBE degradation products, such as TBA (tert-butyl alcohol) and TBF (teri-butyl formate).

Microorganisms capable of co-metabolizing MTBE may be used in methods of decontaminating media (such as soils, water or air) containing MTBE. In the simplest embodiment of this application, a pure culture of the selected microorganism is combined with the contaminated medium in the presence of a gaseous n-alkane or a simple branched alkane (or, a suitable alkane metabolite) as a primary metabolite. In other embodiments, the present invention contemplates the use of biofilters for removing MTBE from a medium. In their basic form, such biofilters comprise a surface for supporting microbial biomass, a pure culture of the selected microorganism provided on the surface to form a microbial biomass, a supply means for supplying a gaseous n-alkane or a simple branched alkane (or a metabolite thereof) to the microbial biomass, and a supply means for supplying a medium containing MTBE to the microbial biomass.

In other aspects of the present invention, microorganisms possessing cytochrome P-450 activities are shown to be capable of co-metabolizing a wide range of xenobiotic compounds. The invention provides a method of degrading a xenobiotic compound which comprises providing a pure culture of a microorganism capable of degrading the xenobiotic compound as a co-metabolite of a gaseous n-alkane or simple branched alkane, providing this culture with a suitable alkane (or a metabolite of the alkane) as a primary metabolite and then contacting the culture with the xenobiotic compound. Xenobiotic compounds which may be degraded include MTBE, TAME, ETBE, DEE, naphthalene, dibenzofuran and chlorinated aliphatic hydrocarbons such as chloroform.

DETAILED DESCRIPTION OF THE INVENTION

I. Definitions

Figure 1:
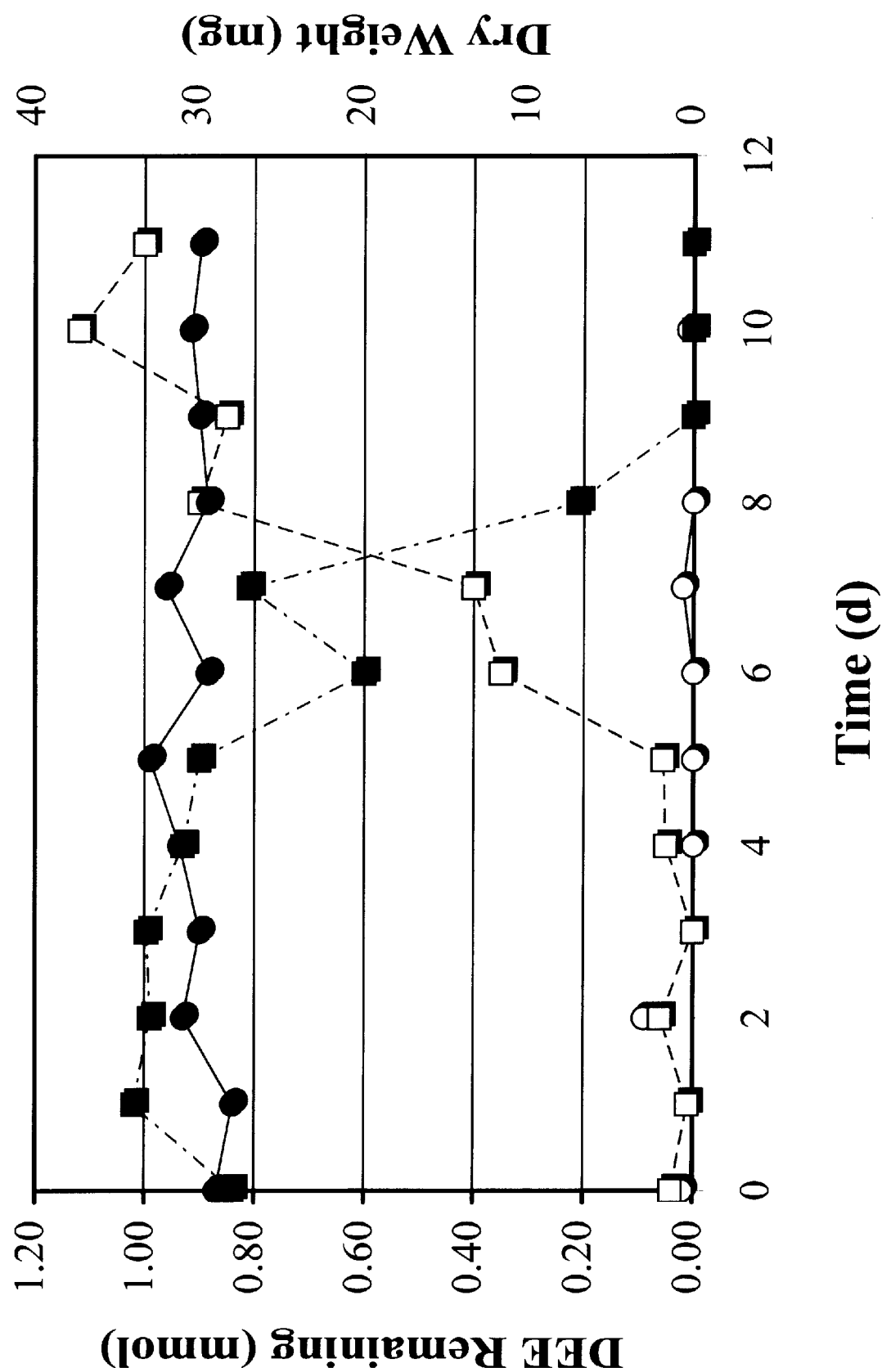
FIG. 1 is a graph showing a time course of diethyl ether consumption and mycelial biomass production. Cultures of Graphium sp. were grown in 24 glass bottles (600 ml) sealed with butyl rubber-lined screw caps. Each bottle containing MS media (100 ml), DEE (1 mmol) and conidia ($1 \times 10^6$). Acetylene (0.5% vol/vol, gas phase) was added to twelve bottles. At the indicated times, the DEE content was determined by gas chromatography for 1 bottle with and 1 bottle without acetylene. The mycelia from these bottles were then harvested to determine biomass production. The Figure shows the time course of DEE consumption (closed symbols) and biomass production (open symbols) for conidia incubated with DEE in the (●,○) presence and (■,✕) absence of acetylene.

N-alkane: a single, unbranched chain of carbon atoms having the general formula $C_nH_{2n+2}$. Gaseous n-alkanes include methane, ethane, propane and n-butane. Gaseous n-alkanes suitable for use in the methods of the present invention include ethane, propane and n-butane.

Metabolites of n-alkane include corresponding alcohols and aldehydes, for example ethanol and ethanal (acetaldehyde), butanol and butanal (butyraldehyde).

Simple branched alkane: A chain of carbon atoms having a single branch and having the general formula $C_nH_{2n+2}$. Examples of simple branched alkanes suitable for use in the present invention include isobutane (2-methyl propane) and isopentane (2-methyl butane).

MTBE: Methyl tert-butyl ether, $(CH_3)_3COCH_3$

DEE: Diethyl ether, $CH_3CH_2OCH_2CH_3$

TBA: tert-butyl alcohol, $(CH_3)_3COH$

TBF: Tert-butyl formate, $(CH_3)_3COCHO$

ATCC: American Type Culture Collection, Rockville, Md.

IMI: International Mycological Institute, Egham, Surrey, U.K.

II. Materials and Methods

A. Materials

Graphium sp. (ATCC 58400) was obtained from the American Type Culture Collection (Rockville, Md.). Diethyl ether (99.9 %, inhibitor-free, spectrophotometric grade), methyl tert-butyl ether (99.8 %), tert-butyl alcohol (99+%) and tert-butyl fornate (99%) and calcium carbide (ca. 80%) (for acetylene generation) were obtained from Aldrich Chemical Co. Inc., (Milwaukee, Wis.). All gases were of the highest purity available and all other chemicals were at least of reagent grade.

B. Methods

1. Growth of Graphium sp.

Stock cultures of Graphium sp. were maintained on potato dextrose agar (PDA) plates at 25° C. under constant illumination. Conidia were harvested from mycelia grown for 6 to 9 days on PDA plates and were used to inoculate liquid suspension cultures and filter-attached cultures. Liquid suspension cultures were grown axenically in 600 ml glass bottles (Wheaton Scientific, Millville, N.J.). The growth medium (100 ml) was either potato dextrose broth (PDB) (24 g/l) or a mineral salts (MS) medium, as described previously (Curry et al., 1996). Bottles were inoculated with conidia ($10^6$) and then sealed with screw caps fitted with butyl rubber septa (Wheaton Scientific, Millville, N.J.). Diethyl ether was added to cultures from a saturated aqueous solution made with sterile MS media. Gaseous hydrocarbon substrates and inhibitors were added to the bottles as an overpressure using syringes fitted with sterile filters (0.25 $\mu$m). Liquid suspension cultures were incubated for 4 days (PDB) or 7 days (MS) at 24° C. in an orbital shaker (125 rpm). For experiments using liquid suspension grown mycelia, cultures were harvested by gentle vacuum filtration and washed with MS medium (3×100 ml). The mycelia were then placed in a fresh culture bottle and resuspended with fresh MS medium. The bottles were then sealed with screw caps fitted with butyl rubber septa.

A complication observed with cultures grown in liquid suspension was that it was often difficult to remove all residual growth medium during the vacuum-based washing procedure described above. An alternative method of cultivation was developed which permitted complete elimination of residual growth substrates by culturing Graphium as mycelia attached to a solid substrate. For this method an aqueous suspension (400 $\mu$l) of conidia ($2.5 \times 10^6$/ml) was pipetted onto sterile glass fiber Whatman GF/A filters (7×4 cm) (Whatman Ltd., England) that had been wetted with either MS medium or potato dextrose broth (PDB). The inoculated filters were then placed on a sterile blotting paper wick saturated with either MS medium or PDB. The filter and wicks were then placed in sterile Petri dishes which were then put in sealed containers (1 l). For mycelia grown on MS medium and gaseous hydrocarbons, substrates were added to the gas phase of the sealed containers to an initial concentration of approximately 10% (vol/vol). For mycelia grown on PDB the gas phase in the sealed containers was air. Irrespective of growth substrate the containers were incubated 4 days at 25° C. under constant illumination. When required for experiments, the filter-attached mycelia were removed from the growth container and shaken gently in air to remove residual gaseous substrates. For all experiments described here the filters were then placed directly into glass serum vials (120 ml) which were then sealed with butyl rubber stoppers and aluminum crimp seals (Wheaton Scientific, Millville, N.J.).

2. Cell-free Extracts and Enzyme Assays

Cell-free extracts of mycelia were prepared as described by Onodera el al. (1989b): 2–6 g of mycelia from 5-day liquid suspension cultures were harvested and washed by vacuum filtration. The mycelia were transferred to a Sorvall Omni-mixer chamber (Newtown, Conn.) and homogenized 90 sec with 5 ml buffer (10 mM $K_2HPO_4$ pH 7.0 containing mannitol (0.3 M), β-mercaptoethanol (4 mM) and $MgCl_2$ (2 mM) at 4° C. The homogenate was filtered through Miracloth (Calbiochem, La Jolla, Calif.), and centrifuged for 10 min at 1,000×g at 4° C. The supernatant was centrifuged again for 20 min at 20,000×g at 4° C., followed by ultracentrifugation in a Beckman Ti 70.1 rotor for 90 min at 105,000×g at 4° C. Alcohol dehydrogenase activity of the resulting supernatant was determined spectrophotometrically by following acetaldehyde-dependent NADH oxidation (Racker, 1966).

3. Analytical Procedures

The degradation of n-alkanes, DEE, and MTBE, and the accumulation of products were all monitored using a gas chromatograph (Shimadzu model GC-8A) (Kyoto, Japan) fitted with a flame ionization detector. A stainless steel column (0.3×122 cm) filled with Porapak Q (60–80 mesh) (Waters Associates, Framingham, Mass.) was utilized at a temperature of 170° C., with a detector temperature of 200° C. Nitrogen was used as carrier gas. Either 100 $\mu$l gas phase or 3 $\mu$l liquid phase samples were analyzed. The chromatograph was interfaced to a Shimadzu model C-R3A integrator. Products generated from DEE and MTBE degradation were identified by coelution with authentic standards. Products observed with MTBE were further confirmed using a Finnigan 4000 GC/MS with a Varian 3400 GC, coupled to a Galaxy 2000 data system. The mass spectrometer was operated in electron impact mode (70 eV) with a source temperature of 140° C. A DB-1 column (0.32 mm×30m) was used with a temperature ramp of 2° C./min from 50–200° C., and a detector temperature of 250° C.

4. Other methods

Yields of mycelia were determined from dry weight measurements (Curry et al., 1996). Liquid suspension cultures were vacuum filtered onto paper filters which had been previously dried and weighed. The mycelia and filters were dried at 65° C. for 24h and reweighed. For filter-attached mycelial cultures, the GF/A filters were similarly dried and weighed.

Protein concentrations of mycelial cell-free extracts were determined by the method of Bradford (1976) using bovine serum albumin as a standard.

III. Results

DEE was observed to support growth of Graphium: mycelial biomass production correlated well with the time course of DEE consumption in batch cultures of Graphium when DEE was present as the sole source of carbon and energy (FIG. 1). In contrast, neither biomass accumulation or DEE consumption occurred in the presence of acetylene (FIG. 1). Similar experiments established that growth of Graphium on DEE was also completely inhibited by the same concentration of ethylene, propylene, propyne and n-butyne (0.5% vol/vol; gas phase) which inhibit growth of Graphium on gaseous n-alkanes (data not shown). Other ether-bonded compounds, including 2-ethoxyethanol, n-propyl ether and MTBE, did not support the growth of Graphium when provided as the sole energy source.

Figure 2:
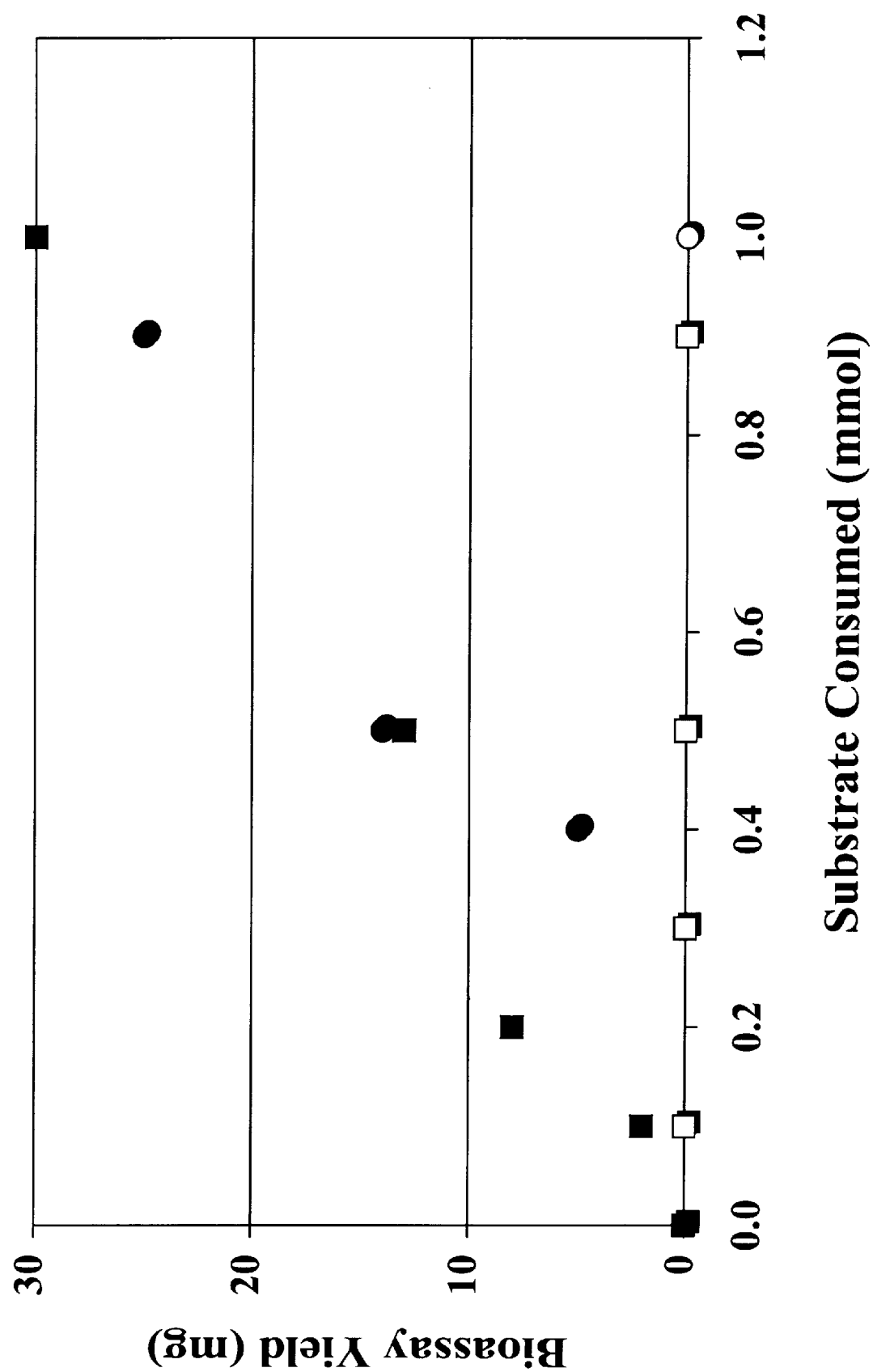
FIG. 2 is a graph showing the growth yield of Graphium on diethyl ether and n-butane. The yield of mycelia from conidia incubated with (■) DEE and (✕) n-butane was determined from dry weight determinations made after complete consumption of the added growth substrate had been confirmed by gas chromatography. The biomass yields obtained for conidia incubated with acetylene (0.5% vol/vol gas phase) and either (●)DEE or (○) n-butane are also shown.
Figure 3:
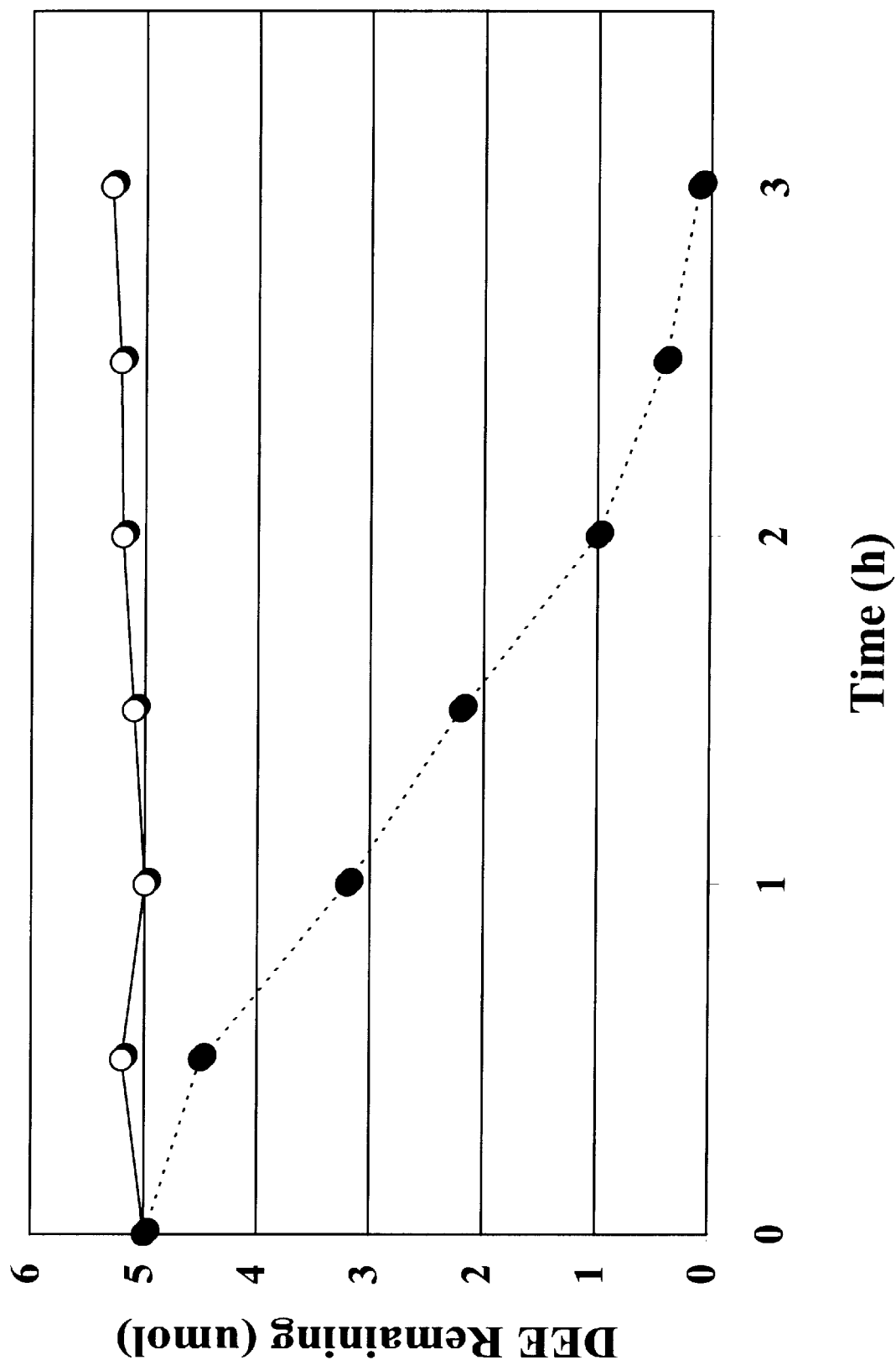
FIG. 3 is a graph showing the degradation of diethyl ether by n-butane grown Graphium. Filter-attached mycelia were grown on n-butane, as described in the Methods. The mycelia (20±2.5 mg dry weight) were incubated in a sealed glass serum vial (120 ml). The reactions were initiated by the addition of DEE (5 μmol), and 100 μl gas phase samples were removed and analyzed by gas chromatography, as described in the Methods. The Figure shows the time course of DEE consumption for mycelia incubated with DEE either (○) with or (●) without acetylene (0.5% vol/vol gas phase).

The molar growth yield for Graphium on DEE was determined using carbon-limited batch cultures in which the biomass was determined after the complete consumption of added DEE had been confirmed by gas chromatography. This yield (28.5 g biomass/mole substrate consumed) was indistinguishable from that determined for n-butane (FIG. 2). It was also observed that filter-attached n-butane-grown mycelia were able to immediately oxidize DEE and that this reaction was inhibited by acetylene (FIG. 3). The maximum rate of DEE oxidation in this experiment was 85 nmole DEE oxidized/hr×(mg dry weight)$^{-1}$. Aqueous suspensions of n-butane- and DEE-grown mycelia also oxidized DEE (10 $\mu$mol) at a very similar initial (0–1 h) rate of 92 (±24) and 90 (±35) nmole/h×(mg dry weight)$^{-1}$, respectively. Similar levels of alcohol dehydrogenase activity were also detected in cell-free extracts of these mycelia (1065 (±15) and 590 (±160) nmole NADH oxidized/min×(mg protein)$^{-1}$ for DEE and n-butane-grown mycelia, respectively). In contrast, DEE was not oxidized by potato dextrose-grown mycelia and extracts of these mycelia did not exhibit significant alcohol dehydrogenase activity (<20 nmole NADH oxidized/min×(mg protein)$^{-1}$). In all experiments using aqueous suspensions of DEE-oxidizing mycelia, no extracellular accumulation of any organic oxidation products from DEE was detected.

Figure 4A:
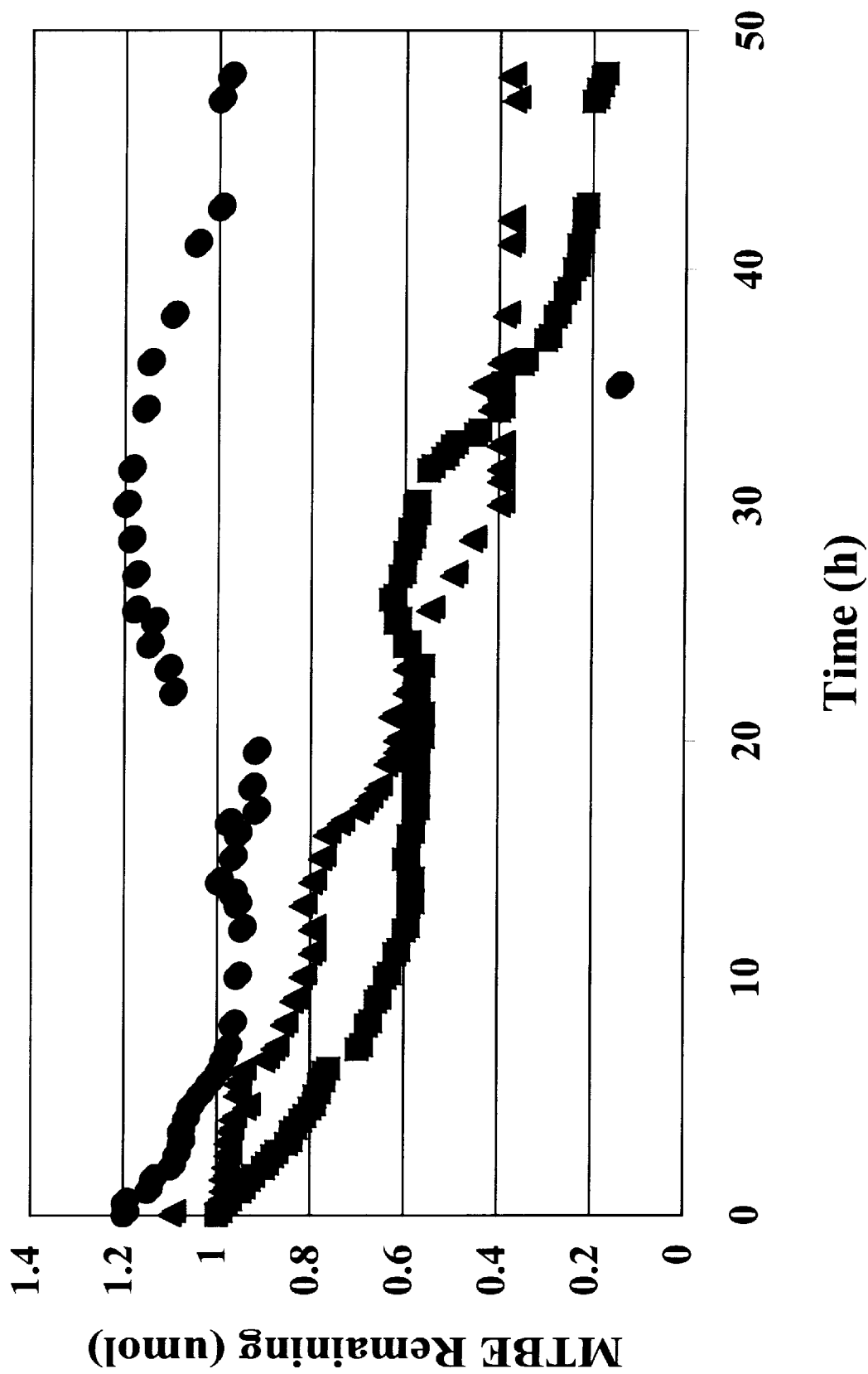
FIG. 4 is a graph showing co-metabolic degradation of methyl tert-butyl ether by n-butane grown Graphium. Filter-attached mycelia of Graphium were grown on n-butane, as described in the Methods. The filters with attached mycelia (40+3 mg dry weight) were transferred to glass vials (120 ml) which were sealed with butyl rubber stoppers and aluminum crimp seals. The reactions were initiated by the addition of MTBE (1 μmol) added from a saturated aqueous solution. Panel A shows the time course for MTBE degradation for mycelia incubated with (●) MTBE and acetylene (0.5% vol/vol gas phase), (▲) MTBE and n-butane (1.0% vol/vol gas phase) and, (■) MTBE alone, with n-butane (0.5% vol/vol gas phase) added after 24 h. The arrow indicates the point at which n-butane was added to this incubation. Panel B shows the corresponding time course for n-butane consumption for mycelia incubated with (_) MTBE and n-butane (1.0% vol/vol gas phase added at t=0 h) and (✕) MTBE and n-butane (0.5% vol/vol gas phase) added after 24 h.
Figure 4B:
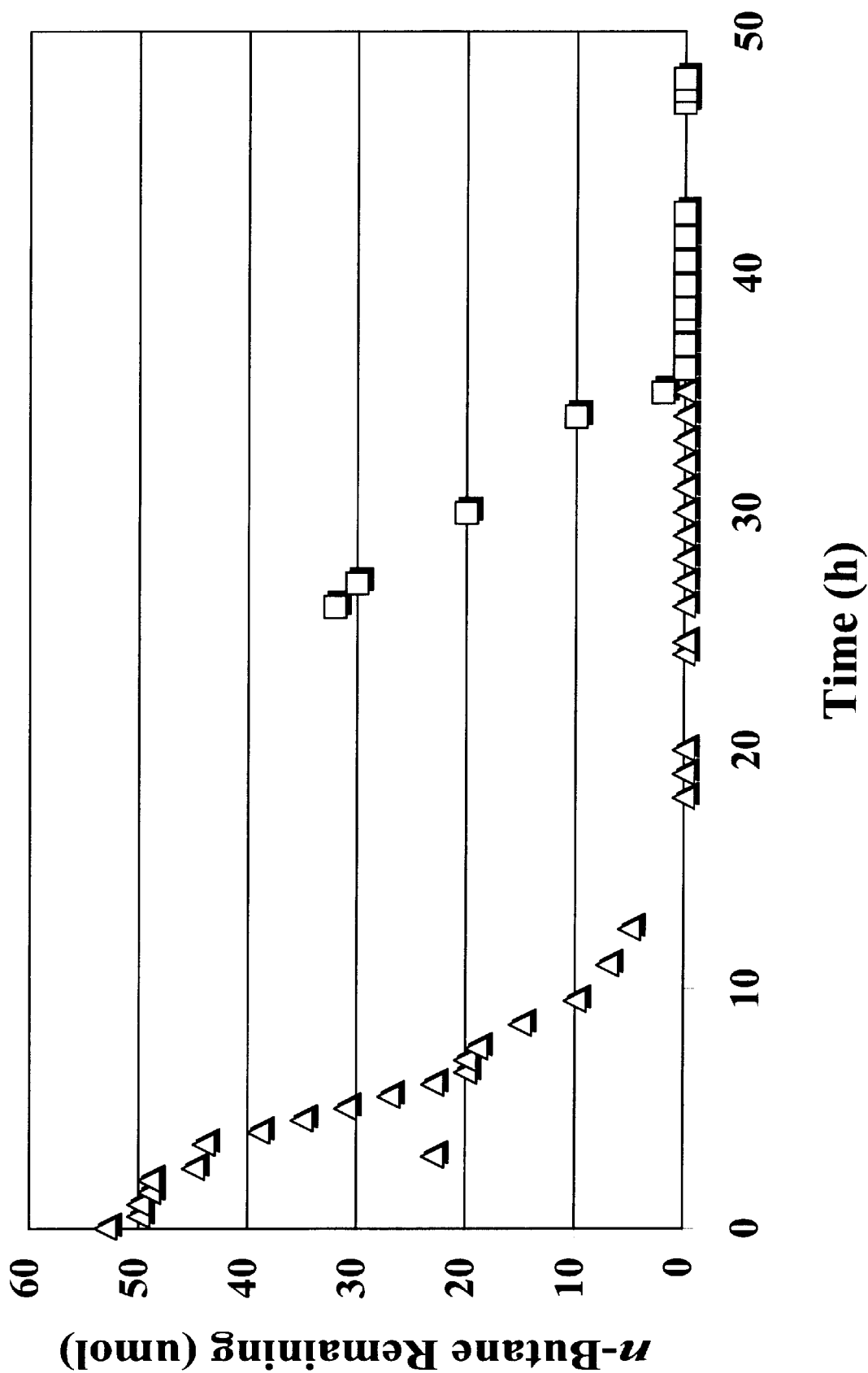

As indicated above, Graphium did not grow with MTBE as a sole source of carbon and energy. However, n-butane-grown mycelia were capable of degrading MTBE (FIG. 4) whereas potato dextrose-grown mycelia did not exhibit this activity (not shown). Degradation of MTBE by n-butane-grown mycelia was fully inhibited by the same concentration of acetylene (FIG. 4), and all other unsaturated hydrocarbons which inactivate n-alkane-oxidizing activity (not shown). These effects indicate that the consumption of MTBE can be attributed to specific enzyme activities rather than non-specific or abiotic processes such as absorption. The presence of n-butane also affected the rate of MTBE degradation (FIG. 4). Mycelia initially incubated without n-butane consumed MTBE faster (1.9 mole/h×(mg dry weight)$^{-1}$) than mycelia initially incubated with n-butane (0.6 nmole/h×(mg dry weight)$^{-1}$). However, the rate of MTBE consumption declined to close to zero for the former mycelia although both MTBE- and n-butane-oxidizing were reinitiated in these mycelia by the addition of n-butane after 24 h. In contrast, MTBE-degrading activity was maintained at an almost constant rate throughout the entire incubation for mycelia initially incubated with n-butane. Ultimately, the quantity of MTBE consumed in both incubations was very similar after 48 h.

Figure 5:
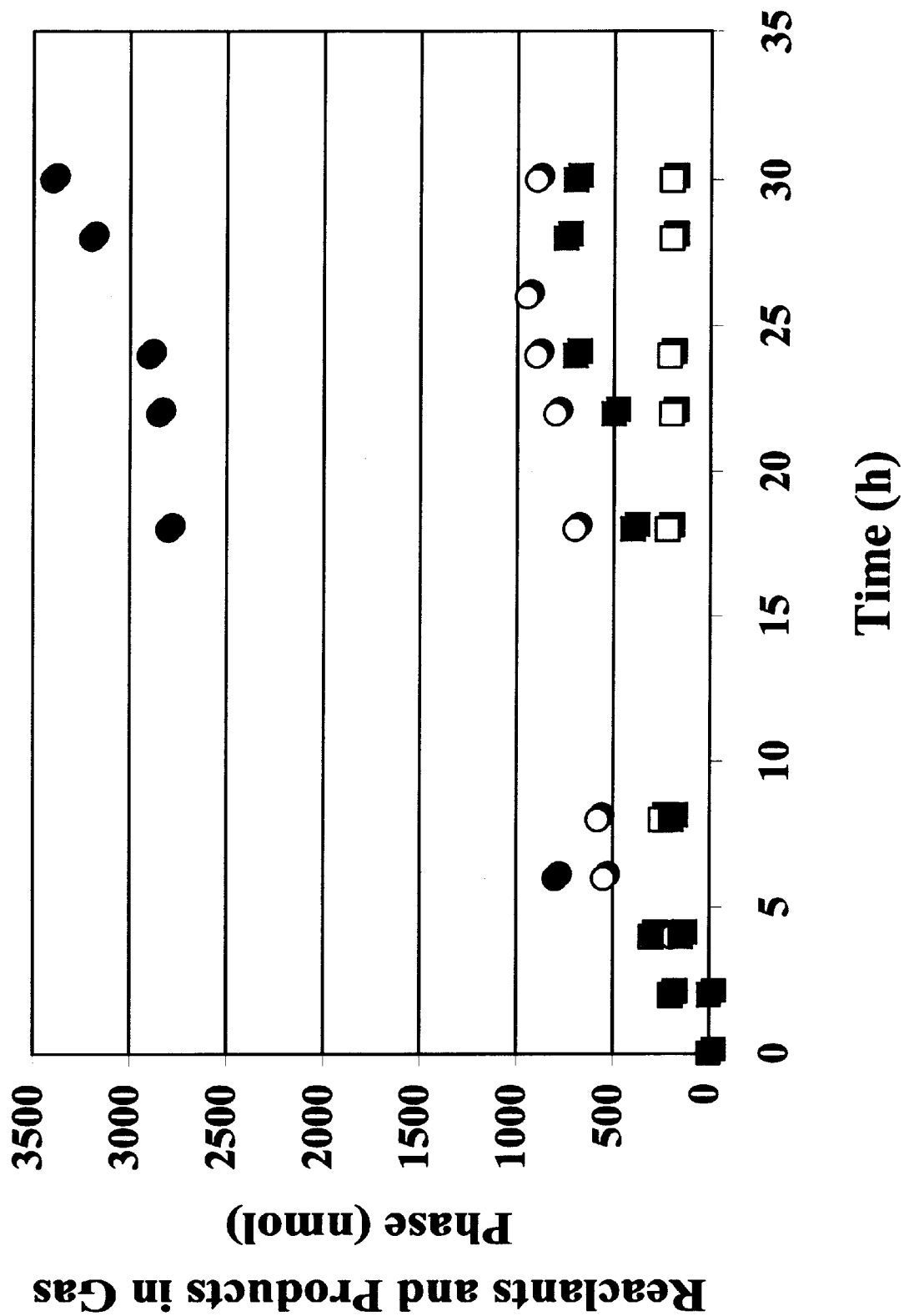
FIG. 5 is a graph showing a time course for tert-butyl formate and tert-butyl alcohol production during methyl tert-butyl ether degradation by n-butane-grown Graphium. Filter-attached mycelia of Graphium were grown on n-butane, as described below. The mycelia (44 mg dry weight) were incubated in a sealed glass serum vial (120 ml). The reactions were initiated by the addition of MTBE (6 μmol) added from a saturated aqueous solution. At the indicated times samples (100 μl) of the gas phase were removed and immediately analyzed by gas chromatography, as described in the Methods. The Figure shows the time course for accumulation of (✕) tert-butyl formate (TBF) and (■) tert-butyl alcohol (TBA) in the gas phase. The symbols (○) and (●) represent the combined quantities of TBF and TBA detected and the total quantity of MTBE degraded, respectively.

In experiments using filter-attached, n-butane-grown mycelia, two MTBE oxidation products were detected: tert-butyl formate (TBF) and tert-butyl alcohol (TBA). The kinetics of TBF and TBA production during MTBE degradation were investigated and the results indicated that TBF production accounted for the large majority of MTBE consumption during the first 3 h of the reaction (FIG. 5). The quantity of detected TBF reached a maximum after 4 h and then declined slowly over the following 24 h of the incubation. In contrast, TBA was not detected during the first 3 h of the incubation but it did accumulate at a nearly constant rate over the remainder of the incubation. The degradation rate for MTBE (6 $\mu$mol) was 4.5 nmole/h×(mg dry weight)$^{-1}$ at the start of the experiment (0–4 h) and this rate had declined to 1.3 nmole/h (mg dry weight)$^{-1}$ at the end of the experiment (24–29 h). This compared to a TBA production rate of 0.47 nmole/h×(mg dry weight)$^{-1}$ over the same period (24–29 h). After 29 h the combined accumulation of TBF and TBA accounted for approximately 30% of the total quantity of MTBE consumed.

The kinetics of TBF and TBA accumulation in this experiment suggest that TBF undergoes further transformations to TBA. The potential for a hydrolytic transformation of TBF was investigated: The rate of hydrolysis of TBF (10 $\mu$mol) was determined over an 8 h period in incubations containing either wetted sterile filters or filters with either n-butane-grown or PDB-grown mycelia. All of the filters contained similar quantities of water (2.2±0.2 g). TBF was hydrolyzed to TBA in all instances. In the absence of biomass, TBF was hydrolyzed at a rate of 79 nmole/h×(g water)$^{-1}$. The presence of mycelial biomass increased this rate by 81 and 8 nmole/h×(mg dry weight)$^{-1}$ for n-butane and PDB-grown mycelia, respectively.

Figure 6:
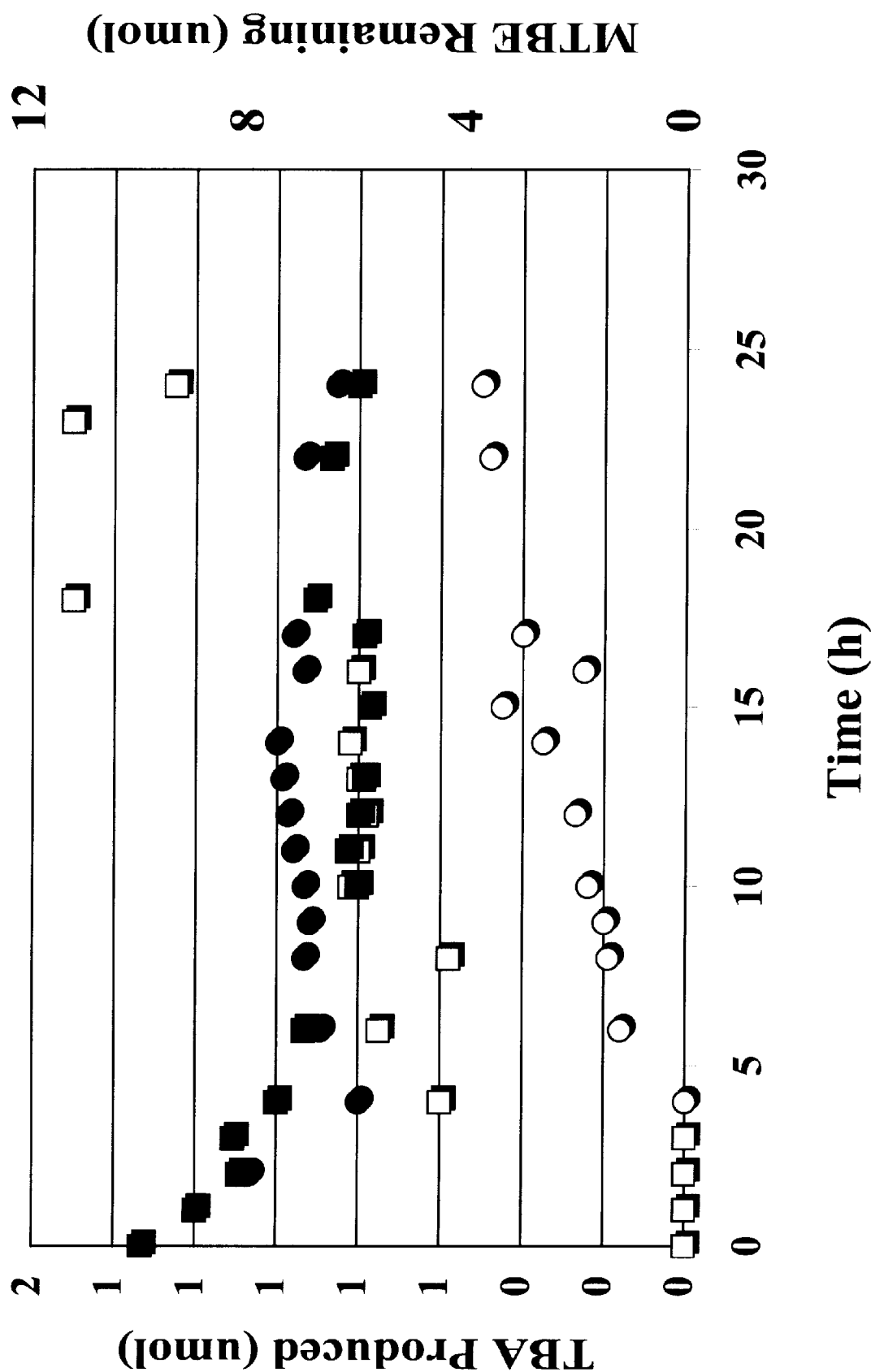
FIG. 6 is a graph showing a time course for methyl tert-butyl ether consumption and tert-butyl alcohol production by Graphium grown on n-butane or diethyl ether. Mycelia of Graphium were grown in liquid culture on either n-butane or DEE, as described in the Methods. The harvested mycelia (50 and 55 mg dry weight for n-butane and DEE-grown mycelia, respectively) were resuspended in MS medium (50 ml) in glass bottles (600 ml) sealed with screw caps and butyl-rubber septa. The reactions were initiated by the addition of MTBE (10 μmol) added from an aqueous saturated solution. The consumption of MTBE and production of tert-butyl alcohol were determined from liquid phase samples (3 μl) immediately analyzed by gas chromatography. The Figure shows the time course for MTBE consumption (closed symbols) and the corresponding time course for tert-butyl alcohol (TBA) accumulation (open symbols) in the reaction medium for (■,✕) n-butane- and (●,○) DEE-grown mycelia.

The ability of other growth substrates to support Graphium MTBE-degrading activity was also investigated. Propane-grown mycelia were able to oxidize MTBE with a higher specific activity (4.5 nmole/h×(mg dry weight)$^{-1}$) than n-butane-grown mycelia (FIG. 4) when incubated in gas phase reactions with an equivalent quantity of MTBE (1 $\mu$mol) (not shown). Overall, the rate of MTBE degradation was found to be highly dependent on the MTBE concentration. The maximum initial rate of MTBE degradation (0–3 h) observed to date (10.5 nmole/h×(mg dry weight)$^{-1}$) was observed with n-butane-grown mycelia incubated with 10 $\mu$mol MTBE in aqueous suspensions (approximately 150 $\mu$M MTBE in solution) (FIG. 6). In this experiment, TBA was the sole MTBE oxidation product detected, although the kinetics of TBA accumulation and the total quantity of degraded MTBE accounted for by TBA production were very similar to those observed in other experiments (FIG. 5). In the experiment described in FIG. 6, mycelia grown on DEE were observed to be able to oxidize MTBE at rates very similar to n-butane-grown mycelia. For DEE-grown mycelia, TBA was also detected as a sole MTBE oxidation product although in this instance total TBA accumulation only accounted for approximately 12% of the total quantity of MTBE degraded after 24 h.

In similar experiments, co-metabolism of TAME has also been demonstrated (data not shown).

IV. Discussion of Results

Figure 7:
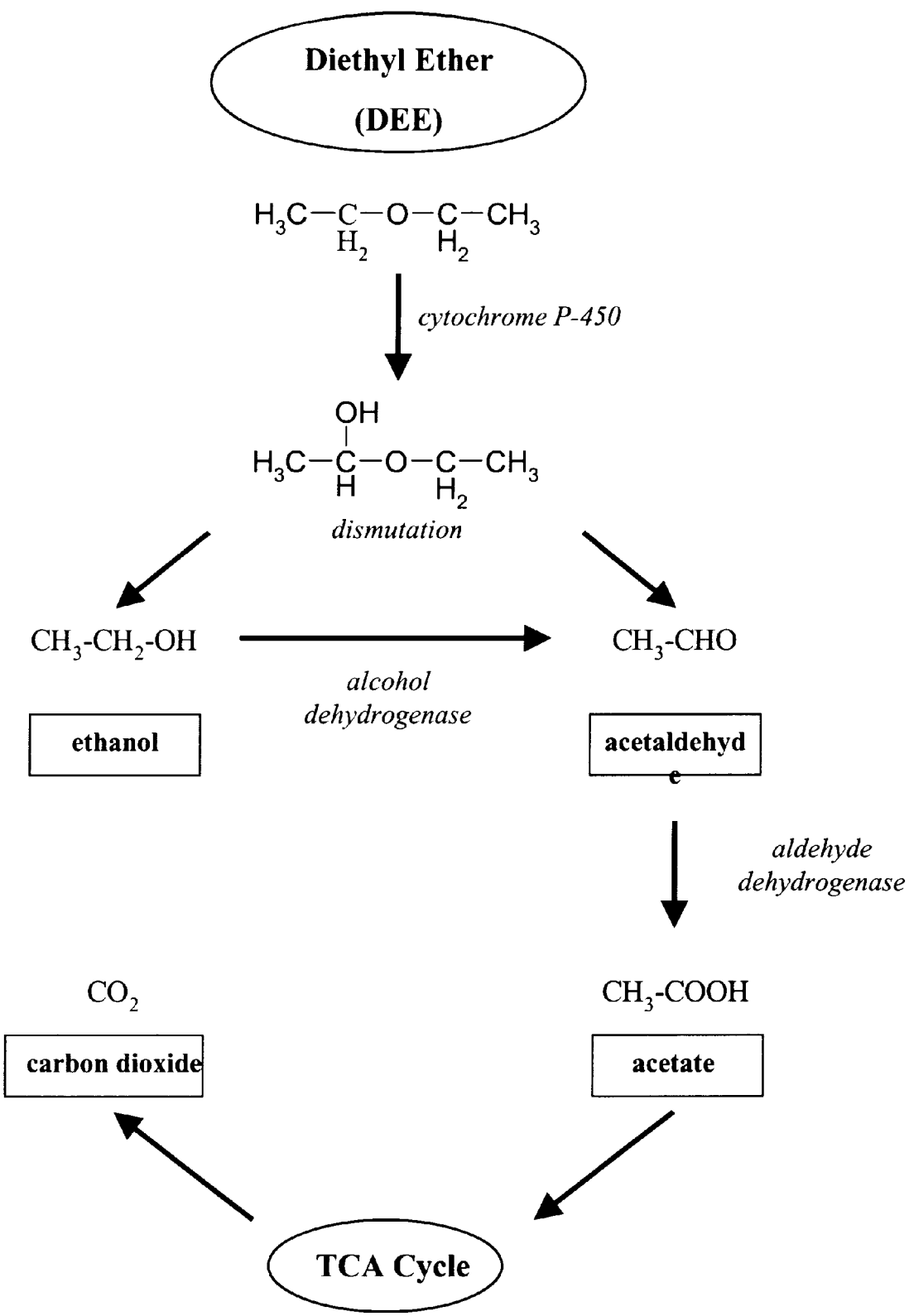
FIG. 7 is a schematic showing a proposed pathway for the metabolism of diethyl ether by Graphium. [ ]-designates proposed hemiacetal intermediates.

The results presented above suggest that MTBE and DEE are oxidized by the same enzyme in Graphium, and that these two reactions are distinguished by the fact that the organism can grow on the products of one reaction, but not the other. In the case of DEE the results suggest that this compound is used directly as a growth-supporting substrate because biomass production correlated well with both the kinetics (FIG. 1) and quantity (FIG. 2) of DEE consumption. The identical sensitivity of n-butane- and DEE-oxidizing activity to inhibition by unsaturated hydrocarbons and the ability of n-butane-grown mycelia to immediately oxidize DEE (FIG. 3) argues that both substrates are initially oxidized by a very similar, if not the same, enzyme. The inability to detect the extracellular accumulation of DEE oxidation products by n-butane grown mycelia in reactions involving aqueous suspensions of mycelia strongly suggests that these compounds are rapidly oxidized by preexisting dehydrogenases and that the pathways of DEE and gaseous n-alkane oxidation are very similar. The essentially identical molar growth yields (FIG. 2) and alcohol dehydrogenase activities observed in DEE- and n-butane-grown mycelia clearly further support this argument. A proposed reaction scheme for the catabolism of DEE, which involves an initial O-dealkylation reaction is presented in FIG. 7. The inability of Graphium to grow on 2-ethoxyethanol (a hydroxylation rather than an O-dealkylation product of DEE) further supports the hypothesis that DEE oxidation involves an initial O-dealkylation reaction which generates ethanol and acetaldehyde.

In considering other possible pathways to account for the growth of Graphium on DEE, it is important to note that the inhibitory effects of acetylene on mycelial growth in the presence of DEE (FIG. 1) eliminates the possibility that growth was supported by contaminants such as ethanol or acetate, since it has been previously established that acetylene does not affect growth on these substrates (Curry et al., 1996). However, the results do not allow the complete elimination of all possible roles for contaminants (such as ethanol) in DEE-dependent growth. For example, it is known that cytochrome P-450 is induced in mammalian systems by both DEE and ethanol. The results presented above do not permit a conclusive determination that the putative cytochrome P-450 activity observed in DEE-grown Graphium is induced by DEE itself: it could be induced by trace ethanol contamination in DEE or by ethanol generated from DEE oxidation by low levels of constitutive cytochrome P-450 activity. However, other experiments in this study have demonstrated that the addition of trace levels of ethanol (50 $\mu$M) to mycelia incubated with n-propyl ether (1 $\mu$mol) does not initiate growth on this ether.

In contrast to DEE degradation, MTBE degradation by n-alkane-grown Graphium is a co-metabolic process in which MTBE is fortuitously oxidized by the same enzyme used to initiate n-alkane and DEE oxidation. This conclusion is supported by several results. First, MTBE degradation occurred immediately after exposing n-alkane-(FIG. 4) and DEE-grown (FIG. 6) mycelia to MTBE and did not occur in potato dextrose-grown mycelia. This indicates that MTBE-degrading activity is selectively expressed when gaseous n-alkanes or DEE are used as growth substrates. Second, MTBE degradation was inhibited by the same concentrations of unsaturated hydrocarbons which inhibit n-alkane and DEE oxidation (FIG. 4). As the results with DEE also suggest that DEE and gaseous n-alkanes are initially oxidized by the same enzyme, it is concluded that DEE, MTBE and gaseous n-alkanes are all oxidized by the same putative cytochrome P-450. Third, the products of MTBE degradation accumulated extracellularly (FIG. 5). This is compatible with a limited catabolism of MTBE and the inability of Graphium to grow on this compound. Fourth, the rate of MTBE degradation by mycelia initially incubated with both n-butane and MTBE was slower than the rate observed for mycelia initially incubated with MTBE alone (FIG. 4). This is compatible with a competitive interaction between n-butane and MTBE for binding to, and oxidation by, the same enzyme. Finally, for mycelia initially incubated with MTBE alone, the MTBE degradation rate progressively declined and was then stimulated following the addition of n-butane (FIG. 4). This is compatible with a progressive exhaustion and subsequent replenishment of reductant required to support cytochrome P-450-catalyzed oxidations. The immediate commencement of n-butane consumption after the addition of n-butane also indicates that the earlier decline in MTBE degradation rate was not due to a toxic effect of previous MTBE degradation. The maximal rate of MTBE degradation observed to date was approximately 10 nmole/h$\times$(mg dry weight)$^{-1}$ of mycelia with liquid suspensions of Graphium exposed to a dissolved MTBE concentration of approximately 150 $\mu$M. Although the dissolved concentration of MTBE cannot be accurately determined in the gas phase experiments, the parallel between the progressive increase in specific rates of MTBE and the quantity of MTBE added in several different experiments suggests that the maximal rate of MTBE degradation by Graphium was not reached. This conclusion is also supported by the fact that the $K_m$ for MTBE in mammalian microsomes ranges from 0.7 to 1.4 mM, depending on the compound used to induce cytochrome P-450 activities (Brady et al., 1990).

Figure 8:
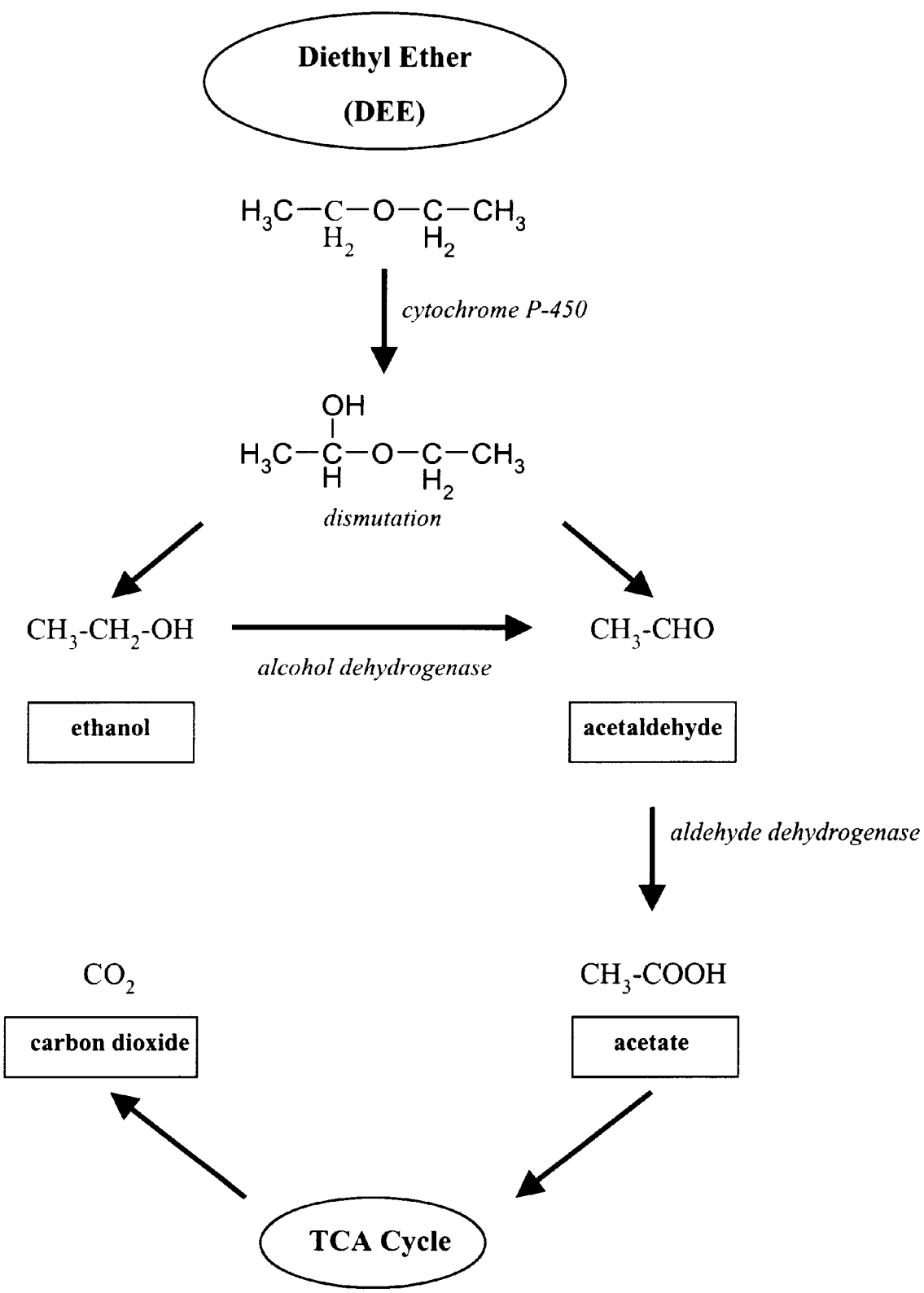
FIG. 8 is a schematic showing a proposed pathway for the metabolism of methyl tert-butyl ether by Graphium. [ ]-designates proposed hemiacetal intermediates.

The principal difference between MTBE and DEE degradation is that Graphium apparently cannot utilize the products of MTBE degradation as both carbon and energy sources to support growth. In mammalian microsomes, MTBE oxidation is currently thought to involve an O-dealkylation reaction which generates TBA and formaldehyde as detectable products (Brady et al., 1990; Mumtaz et al., 1994). This reaction arguably involves an initial hydroxylation of MTBE to tert-butoxymethanol followed by the dismutation of this hemiacetal intermediate (White et al., 1996) (reaction scheme shown in FIG. 8) and is analogous to the reaction proposed for DEE oxidation (see FIG. 7). However, this direct pathway of TBA formation does not agree with the results which indicate that TBF, rather than TBA, is the first detected product of MTBE oxidation. A reasonable explanation of this apparent discrepancy is that tert-butoxymethanol is rapidly oxidized to TBF by the alcohol dehydrogenases which have been shown to be present in MTBE-degrading mycelia. It is further suggested that the resulting TBF then undergoes both biotic and abiotic hydrolysis to yield TBA and the as yet undetected $C_1$ product, formate (FIG. 8).

The results presented herein suggest that the co-metabolism of MTBE by Graphium and other microbial species having a non-specific P-450 cytochrome oxidase could be used for the remediation of MTBE contamination. The previous studies demonstrating the degradation of MTBE by mixed cultures and pure bacterial strains stressed the use of this compound as a growth-supporting substrate, and slow rates of MTBE consumption were described for cultures exposed to MTBE concentrations as high as 200 mg/l (Salanitro et al., 1994 and Mo et al., 1997). However, current environmental levels of MTBE (Squillace et al., 1996) are unlikely to support significant microbial populations and so this could limit the application of growth-based microbial processes for the remediation of environmental MTBE contamination. In contrast, microbial co-metabolic activities are not significantly controlled by the concentration of the target contaminant unless toxic effects arising from the contaminant are observed. Bioremediation schemes involving co-metabolic processes are therefore often suitable for environments with low concentrations of contaminants. Aerobic co-metabolic processes catalyzed by bacteria which express non-specific oxygenases in response to hydrocarbon growth substrates such as methane, propane and toluene have been utilized for the bioremediation of chlorinated hydrocarbons such as trichloroethylene (McCarty, 1993). As filamentous fungi which can utilize gaseous hydrocarbons as growth substrates can be readily isolated from soils (Davies et al., 1973), this present study suggests that a similar process could be envisioned for MTBE degradation by gaseous n-alkane-utilizing fungi either in situ or through more conventional pump-and-treat methodologies.

V. Selection of Microorganisms for MTBE Bioremediation

As noted above, the mechanism proposed herein for the co-metabolism of MTBE by Graphium species is based on the non-specific activity of cytochrome P-450-containing enzymes. This enzyme is proposed to be responsible for the oxidation of the gaseous n-alkanes, as well as MTBE and chlorinated aliphatic hydrocarbons, such as DEE. It is therefore anticipated that a wide range of fungal species which possess such non-specific cytochrome P-450 enzymes will exhibit the ability to co-metabolize MTBE. For example, it is predicted that other alkane-oxidizing fungi will also be able to co-metabolically degrade MTBE.

While the experiments described herein utilized gaseous n-alkanes as the primary metabolite, co-metabolism of MTBE (or TAME or ETBE) by the microorganisms in question may also be accomplished using simple branched alkanes, such as isobutane and isopentane, as well as n-alkane metabolites, such as alcohols or simple acids.

Accordingly, while the above experiments relate to Graphium sp. ATCC 58400, one of skill in the art will appreciate that bioremediation of MTBE may be accomplished using other fungal species. By way of example only, the following fungal species are known to be capable of growing on gaseous n-alkanes and are therefore expected to co-metabolize MTBE, TAME and ETBE: *Phialophora jeanselmei* (ATCC 26272); *Acremonium strictum* (ATCC 36111); *Eupenicillium zonatum* (ATCC 24353); *Cunninghamella echinulata* var. *elegans* (ATCC 36112); *Graphium putrendis* (IMI 151810); and *Penicillium janczewskii* (IMI 151812). This list is not intended to be limiting: the key to the present invention is the discovery that certain microorganisms exhibit the ability to co-metabolize MTBE; any organism which exhibits this activity (as determined by the simple test procedure discussed below) may be useful in bioremediation of MTBE, TAME and ETBE.

In order to determine whether a candidate fungal strain is capable of co-metabolizing MTBE, the assay procedure as described below is followed. The assay is based on the hypothesis that co-metabolic MTBE degradation will be observed when the organisms are grown on gaseous n-alkanes, because these are the conditions when an appropriate cytochrome P-450 enzyme activity is expressed. Thus, the experimental approach recommended is to establish the rate of MTBE consumption for a candidate organism after growth on gaseous n-alkanes and to compare that to the rate observed when the same organism after growth on non-specific media where gaseous n-alkane-oxidizing activity is not expressed. Mycelia of a candidate fungal strain are thus grown as filter-attached cultures as described above for Graphium. Samples of the candidate strain are grown either with gaseous n-alkanes or with sterile air in the gaseous phase. After growth for 5 days, the mycelial mats are placed in sealed 120 ml glass serum vials, sealed with butyl rubber stoppers and aluminum crimp seals, and the reactions initiated by the addition of MTBE (1mol added from a saturated aqueous solution). MTBE degradation is monitored by gas chromatography as described above.

The ability to degrade MTBE may also be found in bacterial species. Although many bacteria appear to initiate the oxidation of n-alkanes using non-heme-containing monooxygenases, cytochrome P-450s are known to exist in a limited number of hydrocarbon-utilizing bacteria. Most attention has focused on the camphor-oxidizing enzyme from *Pseudomonas putida*, however, several actinomycetes utilize cytochrome P-450s for the oxidation of n-alkanes. For example, Corynebacterium 7EIC was first isolated after growth on propane (Kester and Foster, 1963). It was subsequently demonstrated through spectral studies of cell extracts (Cardina and Jurtshuk, 1968) and the purified protein (Cardina and Jursthuk, 1970) that the enzyme responsible for initiating the oxidation of another n-alkane, n-octane, is a soluble cytochrome P-450. Cytochrome P-450 activity has also been implicated in the growth of Acinetobacter on n-octane and the various activities catalyzed by actinomycetes, including O-dealkylating activities of several Nocardia and Streptomyces species (Sariaslani, 1991). Accordingly, in addition to the use of fungal species for MTBE degradation, this invention also encompasses the use of gaseous n-alkane-utilizing bacteria which express a cytochrome P-450 activity for growth substrate oxidation. Such bacterial species are likely to be found among the hydrocarbon-oxidizing actinomycetes in the genera Arthrobacter, Brevibacterium, Nocardia, Mycobacteria and Rhodococcus, and in particular, species such as: Corynebacterium 7EIC (*Rhodococcus rhodochrous*) (ATCC 19067), Rhodcoccus sp. (ATCC 21499), *Brevibacterium butanicum* (ATCC 21196), *Brevibacterium ketoglutamicum* (ATCC 15587), *Arthrohacter rubellus* (ATCC 21495), *Arthrobacter petroleophagus* (ATCC 21494), *Corynebacterium alkanum* (ATCC 21194), *Mycobacterium paraffinicum* (ATCC 12670); *Pseudomonas butanovara* (ATCC 43655); *Xanthobacter autotrophicus* (ATCC 35674); and *Pseudomonas florescens* (ATCC 11253). Again, this list of organisms is not intended to be limiting; the ability of these and other candidate bacteria to co-metabolize MTBE may be readily ascertained by a modification of the assay described above. Essentially, candidate bacteria are grown on standard growth media (such as Luria broth) in the presence of air or on mineral salts medium in the presence of gaseous n-alkanes. MTBE is added to initiate the experiment, and the presence of MTBE degradation products is ascertained by the use of a gas chromatogram as described above.

VI. Incorporation of MTBE Degrading Microorganisms into Treatment Systems

Microorganisms which degrade MTBE may be utilized in bioremediation schemes to remove MTBE from contaminated environments, such as air, soil or water. Various bioremediation schemes may be employed, such as air biofilters for removing MTBE from air, and activated sludge, rotating biological contactors, trickling filters and biofilm reactors for removing MTBE from water or other aqueous media. MTBE-degrading microorganisms may also be directly injected into the ground for decontamination of MTBE-containing soils. In all cases, a gaseous n-alkane or an n-alkane metabolite will be added to the filter system as the primary metabolite.

The essential features of a bioremediation system for MTBE are thus:

a microorganism capable of co-metabolizing MTBE a support surface on which the microorganism can grow a supply of a gaseous n-alkane or simple branched alkane or a metabolite thereof a supply of a medium containing MTBE Preferably, the alkane or alkane metabolite and the MTBE-containing medium are passed over the support on which the microorganism is growing at a rate sufficient to ensure that a majority of the MTBE is removed in a single pass.

Figure 9:
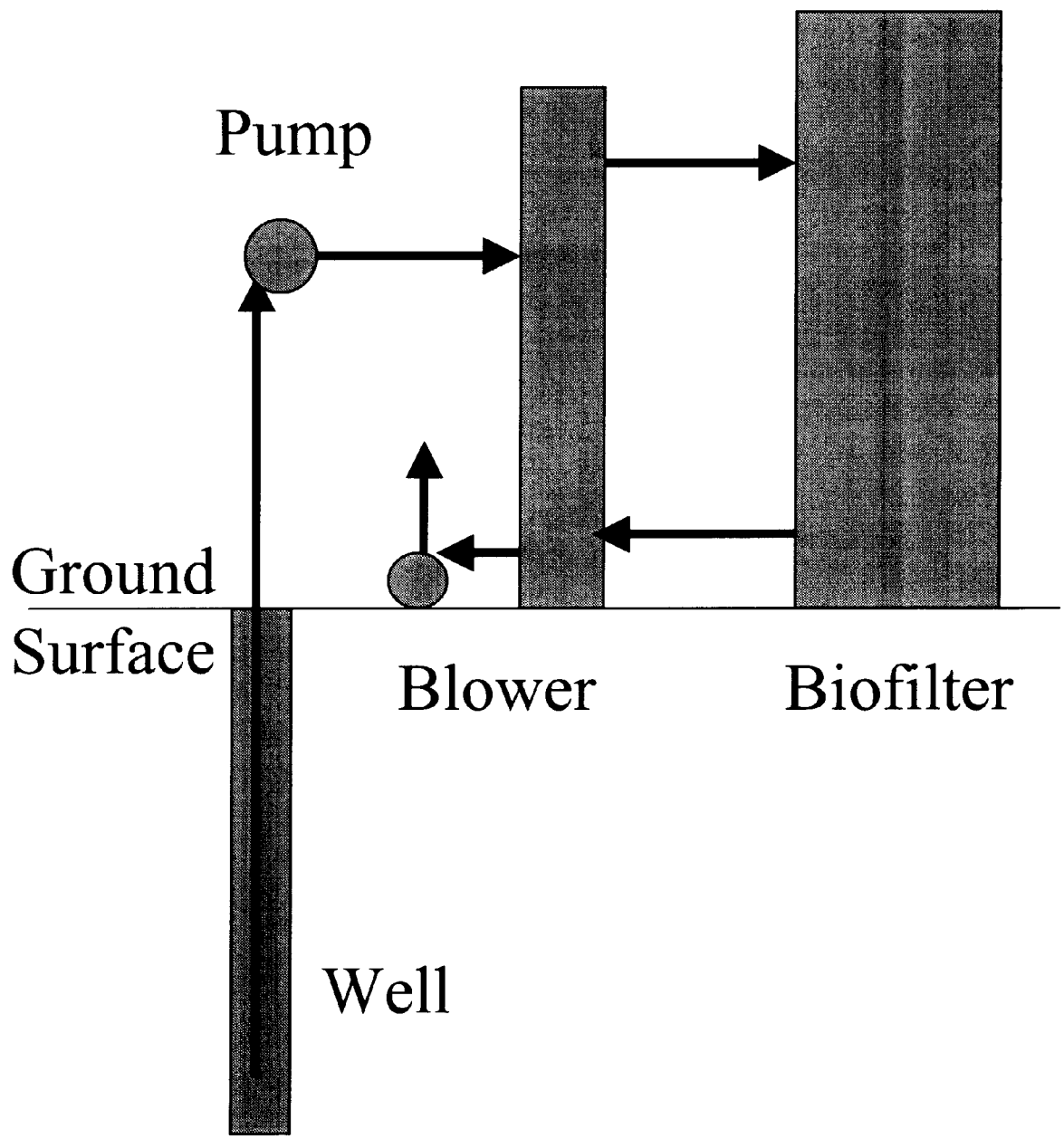
FIG. 9 shows a schematic for an air biofilter.

By way of example only, MTBE may be removed from a contaminated air supply (for example, vapors escaping from a gasoline storage tank, or MTBE removed by soil vapor extracted from contaminated soil) using an air biofilter as shown schematically in FIG. 9. The biofilter is packed with material to provide a support surface for the selected microorganism. Such material may be, for example, moss, peat, clay, gravel or plastic. The microorganism is provided on the support surface, and air containing MTBE is forced through the biofilter. The biofilter is also supplied with a suitable alkane as a primary metabolite, and water is circulated through the column to provide moisture, nitrogen and phosphorous to support microbial growth.

Figure 10:
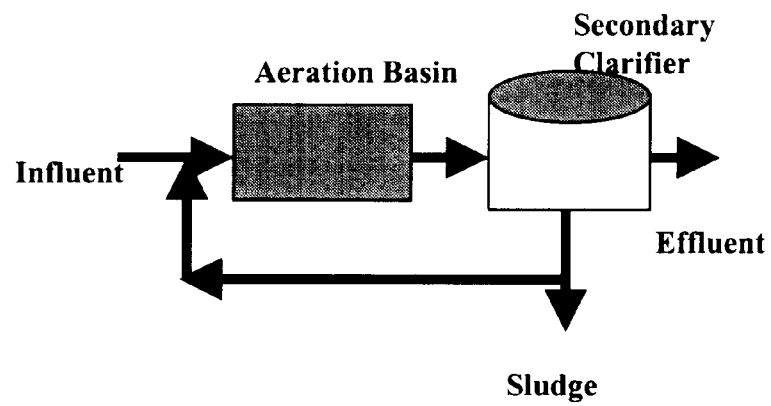
FIG. 10 shows schematics for three types of above-ground treatment systems (activated sludge, rotating biological contactor and biofilm reactor).
Figure 10:
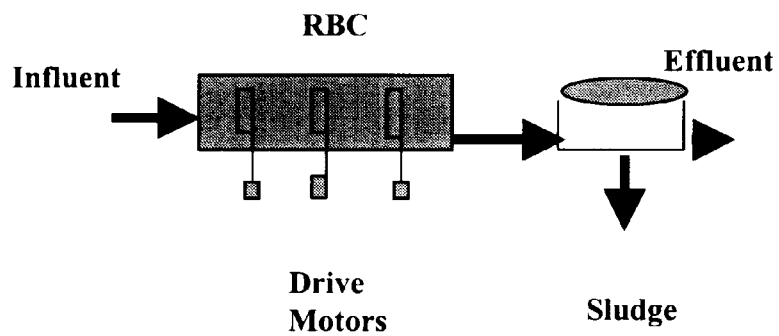
Figure 10:
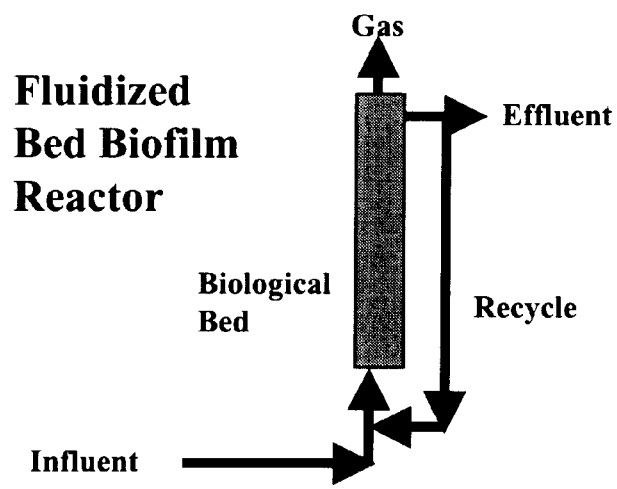

Other forms of biofilter suitable for use in bioremediation of MTBE are shown schematically in FIG. 10.

VII. Bioremediation of Other Xenobiotics

In addition to the bioremediation of MTBE, DEE, TAME and other compounds discussed above, fungal species possessing cytochrome P-450 enzymes have also been demonstrated to co-metabolize naphthalene and dibenzofuran (diphenylene oxide) in the presence of a gaseous n-alkane (data not shown).

Figure 11:
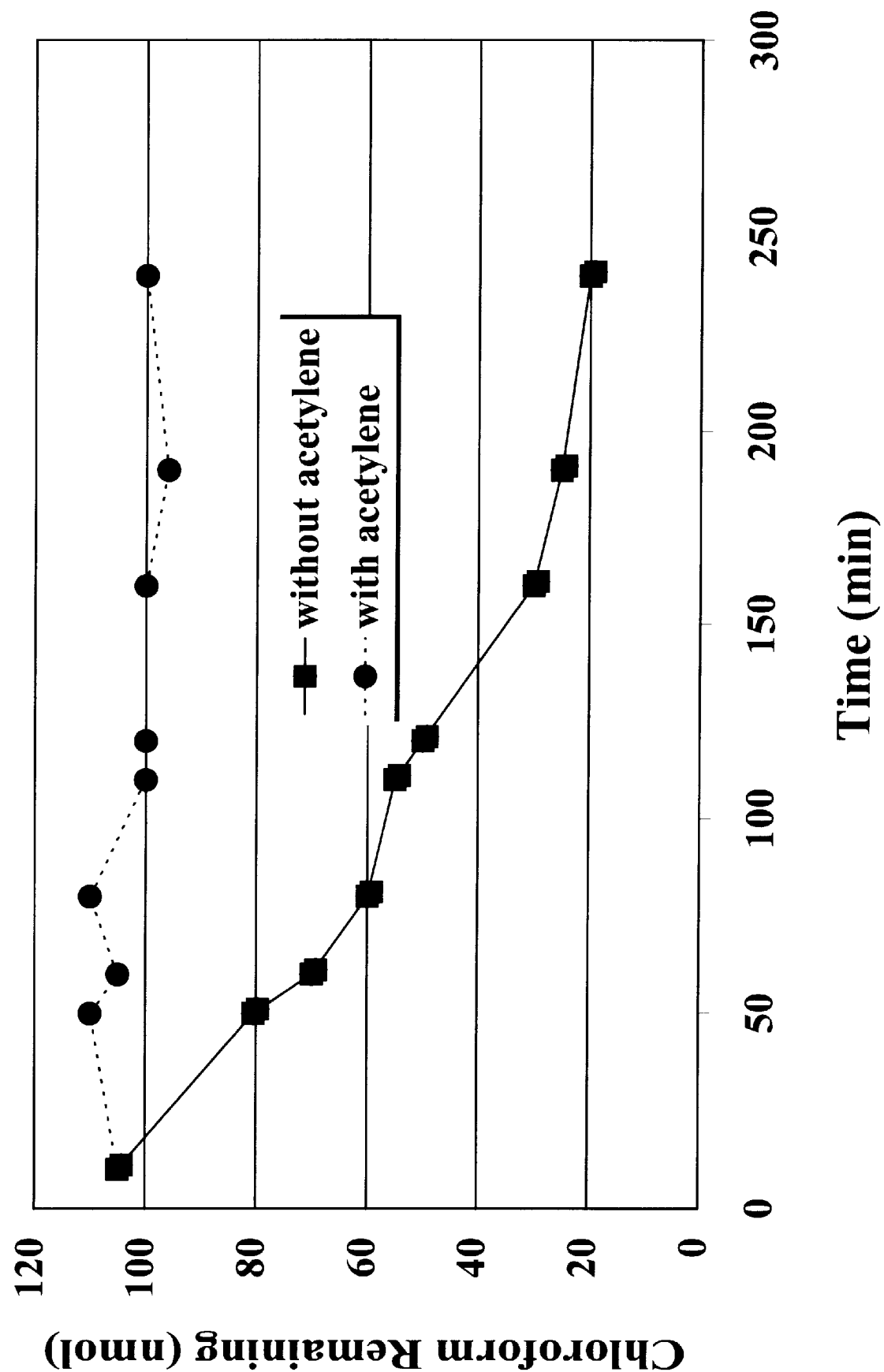
FIG. 11 is a graph showing the metabolism of chloroform by Graphium with and without acetylene.

In addition, fungal species possessing cytochrome P-450 enzymes, such as Graphium sp., have been shown to co-metabolize chlorinated aliphatic hydrocarbons (CAHs) when grown on a gaseous n-alkane (such as butane) as a primary metabolite. A typical result is shown in FIG. 11, which represents an experiment in which the ability of butane-grown Graphium to degrade chloroform was determined in the presence or absence of acetylene. The lack of chloroform degradation in the presence of acetylene is consistent with other results (not shown) indicating that acetylene is a selective mechanism-based inactivator of gaseous n-alkane-induced cytochrome P450 activity. Table I below shows the range of $C_1$ and $C_2$ CAHs that have so far been established to serve as co-metabolism substrates for Graphium.

TABLE 1

Degradation of CAHs (100 nmol) by Graphium.

| Compound | Acronym | Formula | Degradation |
|---|---|---|---|
| Chloromethane | CM | $CH_3Cl$ | – |
| Dichloromethane | DCM | $CH_2Cl_2$ | + |
| Chloroform | CF | $CHCl_3$ | ++ |
| Tetrachloromethane | CT | $CCl_4$ | ND |
| Chloroethane | CA | $C_2H_5Cl$ | + |
| 1,1-Dichlorothane | DCA | $C_2H_4Cl_2$ | – |
| 1,2-Dichloroethane | DCA | $C_2H_4Cl_2$ | ++ |
| 1,1,1-Trichloroethane | TCA | $C_2H_3Cl_3$ | – |
| 1,1,2,2-Tetrachloroethane | TECA | $C_2H_2Cl_4$ | + |

++ = >30% degraded in 4 h; + = <30% degraded in 4 h; – = <5% degraded in 4 h; ND = not determined. All reactions were inhibited by acetylene (0.5%).

These results indicate that microorganisms which possess a cytochrome P-450 enzyme activity may be capable of degrading a wide range of xenobiotic compounds as co-metabolites when grown in the presence of a gaseous n-alkane (or a metabolite of a gaseous n-alkane, such as an alcohol or an aldehyde) as a primary metabolite. Xenobiotic compounds which may be successfully degraded in this way include MTBE, TAME, ETBE, DEE, naphthalene, dibenzofuran and chlorinated aliphatic hydrocarbons, such as chloroform.

VIII. References

Ainsworth, S. J. (1991). Chem. Eng. News (Jun. 10, 1991) pp. 13–16.

Alexander, M. (1973). Biotechnol. Bioeng. 15: 611–647.

Arciero et al. (1989). Biochem. Biophys. Res. Commun. 159: 640–643.

Bradford, M. (1976). Anal. Biochem. 72: 248.

Brady et al. (1990). Arch. Toxicol. 64: 157–160.

Brady et al. (1988). Mol. Pharmacol. 33: 148–154.

Cardina, G., and P. Jurtshuk (1968). J. Biol. Chem. 243: 6070–6072.

Cardina, G., and P. Jurtshuk (1970). J. Biol. Chem. 245: 2789–2796.

Chenglis, C. P., and R. A. Neal. (1980). Biochem. Pharmacol. 29: 247–248.

Colby et al. (1977). Biochem. J. 165: 395–402.

Curry et al. (1996). Appl. Environ. Microbiol. 62: 2198–2200.

Dabrock et al. (1992). Arch. Microbiol. 158: 9–13.

Dalton, H., and D. I. Stirling. (1982). Phil Trans. R. Soc. Lond. B 297: 481–496.

Davies, J. S., A. M. Wellman, and J. E. Zajic. (1973). Can. J. Microbiol. 19: 81–85.

Davies, J. S., J. E. Zajic, and A. M. Wellman. (1974). Dev. Ind. Microbiol. 15: 256–262.

Davies, J. S., A. M. Wellman, and J. E. Zajic. (1976). Appl. Environ. Microbiol. 32: 14–20.

De Biasi et al. (1992). Chem-Biol Interact 85: 229–242.

Ensign, S.A., M.R. Hyman, and D.J. Arp. (1992). Appl. Environ. Microbiol. 58: 3038–3046.

Ewers, J., D. Frier-Schroder, and H-J Knackmuss (1990). Arch Microbiol. 151: 410–413.

Folson, B. R., P. J. Chapman, and P. H. Pritchard (1990). Appl. Environ. Microbiol. 56: 1279–1285.

Foster, (1955) In: Perspectives and Horizons in Microbiology (Wakesan, S. A., (ed.)), Rutgers University Press, New Brunswick.

Harker, A. R., and Y. Kim. (1990). Appl. Environ. Microbiol. 56: 1179–1181.

Hazeu. W. (1975). Antonie van Leeuwenhoek. 41: 121–134.

Heyden, M. T. (1974). Proc. Soc. Gen. Microbiol. 81: ix-x.

Horvarth, R. S. (1972). Bacteriol. Rev. 36: 146–155.

Hou et al. (1984) Dev. Ind Microbiol. 24: 477–482.

Hyman, M. R., and D. J. Arp (1988). Anal. Biochem. 173: 207–220.

Hyman, M. R., I. B. Murton, and D. J. Arp (1988). Appl. Environ. Microbiol. 54: 3187–3190.

Jezequel, S. G., B. Kaye, and I. J. Higgins. (1984). Biotechnol. Lett. 6: 567–570.

Kester, A. S., and J. W. Foster (1963) J. Bacteriol. 85: 859–869.

Malachowsky et al. (1994) Appl. Environ. Microbiol. 60: 542–548.

Mausersberger, S., W.-H. Schunch, and H.-G. Mueller (1981) Z. Allegem. Mikrobiol. 21: 313–321.

Mays, M. A. (1989). Pure Appl. Chem 61: 1373–1378.

McCarty, P. L. (1993). Curr. Opinion Biotechnol. 4: 323–330.

McClay, K., B. G. Fox, and R. J. Steffan (1996). Appl. Environ. Microbiol. 62: 2716–2722.

McLee, A. G., A. C. Kormendy, and M. Wayman. (1972). Can. J. Microbiol. 18: 1191–1195.

Mo et al. (1997) Appl. Microbiol. Biotechnol. 47:69–72.

Mormille, M. R., S. Liu, and J. M. Suflita. (1994). Env. Sci. Technol. 28: 1727–1732.

Mumtaz, M., R. Neft, and S. Wilbur. (1994). United States Department of Health and Human Services Report, Washington, D.C.

Murray, W. D., and M. Richardson (1993). Crit. Rev. Envir. Sci. Technol. 23: 195–217.

Oldenhuis et al. (1991). Appl. Environ. Microbiol. 57: 7–14.

Omura, T. and R. Sato (1964). J. Biol. Chem. 239: 2370–2378

Onodera, M., Y. Endo, and N. Ogasawara. (1989a). Agric. Biol. Chem. 53: 1431–1432.

Onodera, M., Y. Endo, and N. Ogasawara. (1989a). Agric. Biol. Chem. 53: 1947–1951.

Onodera, M., Y. Endo, and N. Ogasawara. (1989b). Agric. Biol. Chem. 53: 2673–2677.

Ooyama, J., and J. W. Foster (1965). Antonie van Leeuwenhoek 31: 45–65.

Ortiz de Montellano, P. R. (1985). In Bioactivation of Foreign Compounds, (Anders, M. (ed.)), pp. 121–155, Academic Press, New York.

Parales et al. (1994). Appl. Environ. Microbiol. 60: 4527–4530.

Patel et al. (1982). Appl. Environ. Microbiol. 44: 1130–1137.

Perry, J. J. (1980). Adv. Appl. Microbiol. 26: 89–115.

Pohl et al. (1997). Biochem. Biophys. Res. Commun. 79: 684–691.

Racker, E. (1966). Methods Enzymol. 79: 500–503.

Raj, H. G., M. Saxena, and A. Allameh (1992). In: Handbook of Applied Mycology. Vol. 4., pp. 881–904, Marcel Dekker Inc., New York.

Raj, H. G., M. Saxena, and A. Allameh (1992). In: Handbook of Applied Mycology (Arora, D. K., R. P. Elander, and K. G. Mukerji, (eds.)), Marcel Dekker Inc., New York.

Rasche, M. E., M. R. Hyman, and D. J. Arp (1991). Appl. Environ. Microbiol. 57: 2986–2994.

Remmer et al. (1984). Xenobiotica 14: 207–209.

Salanitro et al. (1994). Appl. Environ. Microbiol. 60: 2593–2596.

Salmon, A. G., R. B. Jones, and W. C. Mackrodt (1981). Xenobiotica 11: 723–734.

Sariaslani, F. S. (1991). Adv. Appl. Microbiol. 36: 133–178.

Smith et al. (1991). Int. J. Chem. Kinet. 23: 907–924.

Squillace et al. (1996). Env. Sci. Technol. 30: 1721–1730.

Steffan et al. (1997) Appl. Environ. Microbiol. 63: 4216–4222.

Stevenson, P. M., R. T. Ruettinger, and A. J. Fulco (1983). Biochem. Biophys. Res. Commun. 112: 927–934.

Stirling, D. I., and H. Dalton. (1980). J. Gen. Microbiol. 116: 277–283.

Suniari et al. (1984). J. Bacteriol. 160: 1037–1040.

Testai et al. (1991). Toxicol. Lett. 57: 19–27.

Thomas, P. E., D. Ryan, and W. Levin (1976). Anal. Bioch. 75: 168–176.

United States Environmental Protection Agency (1995). Office of Water, Washington, D.C.

Vaz, A. D. N., and M. J. Coon (1987). Proc. Natl. Acad. Sci. USA 84: 1172–1176.

Volesky, B. and J. E. Zajic (1970). Dev. Ind. Microbiol. 11: 184–195.

Wackett, L. P., and D. T. Gibson (1988). Appl. Environ. Microbiol. 54: 1703–1708.

White, G. F., N. J. Russell, and E. C. Tidswell. (1996). Microbiol. Rev. 60: 216–232.

van den Wijngaard et al. (1993). Appl. Environ. Microbiol. 59: 2777–2783

Wilkinson, J. F. (1971). Proc. 21st Symp. Soc. Gen. Microbiol., Cambridge University Press.

World Health Organization (1994) Environmental Health Criteria 163: Chloroform, World Health Organization, Geneva.

Wyndham, R. C. (1986). Can. J. Microbiol. 33: 1–5.

Yeh, C. K., and J. T. Novak. (1994). Water. Env. Res. 66: 744–752.

Zajic, J. E., B. Volesky, and A. Wellman. (1969). Can. J. Microbiol. 15: 1231–1236.

What is claimed is:

1. A method of degrading MTBE comprising:
   (a) providing a pure culture of a Graphium species fungus capable of degrading MTBE as a co-metabolite of a gaseous n-alkane or a simple branched alkane;
   (b) providing the culture with a gaseous n-alkane, a simple branched alkane or a metabolite thereof; and
   (c) contacting the culture with MTBE.

2. The method of claim 1 wherein the gaseous n-alkane or simple branched alkane is selected from the group consisting of: ethane, propane, n-butane, n-pentane, isobutane and isopentane.

3. The method of claim 1, wherein the fingal species is selected from the group consisting of: Graphium sp. (ATCC 58400); Graphium cuneiferum (ATCC 26545); and Graphiumputrendis (IMI 151810).

4. A method of selecting a Graphium species fungus for use in bioremediation of an MTBE-contaminated medium, the method comprising:
   (a) growing a pure culture of the Graphium species fungus in a suitable growth medium;
   (b) supplying the Graphium species fungus with a sufficient amount of at least one gaseous n-alkane or simple branched alkane, or a metabolite thereof;
   (c) adding MTBE to the growth medium;
   (d) assaying the growth medium to quantify MTBE degradation; and
   (e) selecting a Graphium species fungus which degrades MTBE.

5. The method of claim 4 wherein the assaying step is performed by detecting the presence of MTBE degradation products.

6. A method of degrading MTBE, the method comprising the steps of:
   (a) providing a Graphium species fungus selected according to claim 4;
   (b) growing the Graphium species fungus on a suitable growth surface;
   (c) providing the Graphium species fungus with a sufficient supply of a gaseous n-alkane or simple branched alkane or a metabolite thereof; and
   (d) supplying MTBE to the Graphium species fungus.

7. A method of degrading a xenobiotic compound comprising the steps of:
   (a) providing a pure culture of a Graphium species fungus capable of degrading the xenobiotic compound as a co-metabolite of a gaseous n-alkane simple branched alkane or a metabolite thereof;
   (b) providing the culture with a gaseous n-alkane, simple branched alkane or a metabolite thereof; and
   (c) contacting the culture with the xenobiotic compound.

8. The method of claim 7 wherein the xenobiotic compound is selected from the group consisting of: MTBE, TAME, ETBE, DEE, naphthalene, dibenzofuren and chlorinated aliphatic hydrocarbons.

* * * * *

UNITED STATES PATENT AND TRADEMARK OFFICE
CERTIFICATE OF CORRECTION

PATENT NO. : 6,194,197 B1 Page 1 of 1
DATED : February 27, 2001
INVENTOR(S) : Michael R. Hyman, Kenneth Williamson and Lynda M. Ciuffetti It is certified that error appears in the above-identified patent and that said Letters Patent is hereby corrected as shown below:

<u>Title page,</u>
Item [56], OTHER PUBLICATIONS, the following reference should appear as
-- Salanitro et al., "Isolation of a Bacterial Culture that Degrades Methyl t-Butyl Ether," *Applied and Environmental Microbiology*, 60:2593-2596, 1994. --

<u>Column 2,</u>
Line 42, "(teri-" should read -- tert- --.

<u>Column 3,</u>
Line 20, "(■, ¤)" should read --(■,□)--.

Lines 25 and 59, "(¤)" should read --(□)--.

<u>Column 4,</u>
Line 5, "(¤)" should read --(□)--.

Line 27, "(■, ¤)" should read --(■,□)--.

<u>Column 5,</u>
Line 7, "fornate" should read -- formate --.

<u>Column 14,</u>
Lines 28 and 42, "Appl." should read -- Appl. --.

<u>Column 16,</u>
Line 17, "Fingal" should read -- fungal --.
Line 21, "Graphiumputrendis" should read -- *Graphium putrendis* --.

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,194,197 B1  
DATED        : February 27, 2001  
INVENTOR(S)  : Hyman et al.

It is certified that error appears in the above-identified patent and that said Letters Patent is hereby corrected as shown below:

Column 1,
Line 8, the following heading and paragraph should appear:

-- ACKNOWLEDGMENT OF GOVERNMENT SUPPORT

This invention was made with government support under EPA Grant No. R823426-01. The government has certain rights in this invention. --

Column 11,
Line 55, "Jursthuk" should read -- Jurtshuk --.

Column 13,
Line 12, "P450" should read -- P-450 --.
Line 26, "Dichlorothane" should read -- Dichloroethane --.

Signed and Sealed this

Eighth Day of July, 2003

JAMES E. ROGAN  
*Director of the United States Patent and Trademark Office*